（12）United States Patent
Meng et al.

(10) Patent No.: US 12,367,576 B2
(45) Date of Patent: Jul. 22, 2025

(54) ULTRASONIC IMAGING METHOD, ULTRASONIC IMAGING SYSTEM, AND NON-TRANSITORY COMPUTER-READABLE MEDIUM

(71) Applicant: GE Precision Healthcare LLC, Wauwatosa, WI (US)

(72) Inventors: Yuanlong Meng, Wuxi (CN); Hui Ning, Wuxi (CN); Feng Wu, Wuxi (CN); Gang Liu, Wuxi (CN); Yao Ding, Wuxi (CN); Wei Ji, Wuxi (CN)

(73) Assignee: GE Precision Healthcare LLC, Wauwatosa, WI (US)

(*) Notice: Subject to any disclaimer, the term of this patent is extended or adjusted under 35 U.S.C. 154(b) by 108 days.

(21) Appl. No.: 18/069,569

(22) Filed: Dec. 21, 2022

(65) Prior Publication Data

US 2023/0215000 A1    Jul. 6, 2023

(30) Foreign Application Priority Data

Dec. 31, 2021   (CN) .......................... 202111668039.7

(51) Int. Cl.
*A61B 8/00* (2006.01)
*A61B 8/08* (2006.01)
(Continued)

(52) U.S. Cl.
CPC ............ *G06T 7/0012* (2013.01); *A61B 8/463* (2013.01); *A61B 8/5223* (2013.01); *A61B 8/54* (2013.01);
(Continued)

(58) Field of Classification Search
CPC ................... G06T 7/0012; G06T 3/40; G06T 2207/10132; G06T 2207/30004; G06T 2207/30204; A61B 8/463; A61B 8/5223; A61B 8/54; A61B 8/523; A61B 8/461; A61B 8/465; A61B 8/466; A61B 8/483; A61B 8/469; A61B 8/5215
See application file for complete search history.

(56) References Cited

U.S. PATENT DOCUMENTS

2008/0249407 A1   10/2008   Hill
2008/0255448 A1   10/2008   Zhu
(Continued)

OTHER PUBLICATIONS

Tajbakhsh et al (Convolutional Neural Networks for Medical Image Analysis: Full Training or Fine Tuning? IEEE Transactions on Medical Imaging. 35(5):1299-1312, 2016) (Year: 2016).*

*Primary Examiner* — Alexei Bykhovski (57) ABSTRACT

Provided in the present application is an ultrasonic imaging method, including: generating a plurality of anatomical plane schematics, and causing a display to display the same, each one of the plurality of anatomical plane schematics respectively corresponding to a different anatomical plane of interest; acquiring an ultrasonic image of the anatomical plane of interest; and automatically generating an ultrasonic image thumbnail of the anatomical plane of interest, automatically replacing the anatomical plane schematic corresponding to the anatomical plane of interest with the ultrasonic image thumbnail, and causing the display to display the same. Also provided in the present application are an ultrasonic imaging system and a non-transitory computer-readable medium.

20 Claims, 6 Drawing Sheets

(51) Int. Cl.
 *G06T 3/40* (2024.01)
 *G06T 7/00* (2017.01)
(52) U.S. Cl.
 CPC ...... *G06T 3/40* (2013.01); *G06T 2207/10132* (2013.01); *G06T 2207/30004* (2013.01); *G06T 2207/30204* (2013.01)

(56) References Cited

U.S. PATENT DOCUMENTS

| | | | |
|---|---|---|---|
| 2009/0076384 | A1 | 3/2009 | Saad |
| 2016/0295208 | A1* | 10/2016 | Beall ..................... G06V 20/52 |
| 2018/0322627 | A1 | 11/2018 | Gerard |
| 2019/0155836 | A1* | 5/2019 | Kozuka .................. G16H 30/40 |
| 2019/0388060 | A1* | 12/2019 | Aase .................... A61B 8/4444 |
| 2021/0027883 | A1 | 1/2021 | Kumar |
| 2023/0066948 | A1* | 3/2023 | Bharat .................... A61B 8/54 |

* cited by examiner

ULTRASONIC IMAGING METHOD, ULTRASONIC IMAGING SYSTEM, AND NON-TRANSITORY COMPUTER-READABLE MEDIUM

CROSS-REFERENCE TO RELATED APPLICATION

This application claims priority to Chinese patent application number 202111668039.7, filed on Dec. 31, 2021, the entirety of which is incorporated herein by reference.

TECHNICAL FIELD

The present invention relates to the field of ultrasonic imaging and, in particular, to an ultrasonic imaging method, an ultrasonic imaging system, and a non-transitory computer-readable medium.

BACKGROUND

Ultrasonic imaging techniques utilize a probe to perform ultrasonic scanning on a location to be scanned. The probe sends an ultrasonic signal to the location to be scanned, and receives an ultrasonic echo signal. An ultrasonic imaging system processes the echo signal to acquire an ultrasonic image of the location to be scanned. On the basis of this principle, ultrasonic imaging is suitable for real-time, non-destructive scanning performed on a location to be scanned.

Ultrasonic imaging can be used for scanning in a variety of scenarios, for example, scanning performed on the heart, fetus, kidney, etc. In many scanning scenarios, a scanning operator follows a certain scanning standard. That is, ultrasonic images of a plurality of standard anatomical planes need to be acquired, so that comprehensive, accurate imaging can be performed on a location to be scanned. The process of acquiring ultrasonic images of standard anatomical planes is typically cumbersome. On the one hand, the scanning operator needs to ensure that ultrasonic images of required anatomical planes are acquired and stored. On the other hand, the scanning operator needs to ensure that the stored ultrasonic image has acceptable quality. This results in a complex workload.

SUMMARY

The aforementioned deficiencies, disadvantages, and problems are solved herein, and these problems and solutions will be understood through reading and understanding of the following description.

Provided in some embodiments of the present application is an ultrasonic imaging method, comprising: generating a plurality of anatomical plane schematics, and causing a display to display the same, each one of the plurality of anatomical plane schematics respectively corresponding to a different anatomical plane of interest; acquiring an ultrasonic image of the anatomical plane of interest; and automatically generating an ultrasonic image thumbnail of the anatomical plane of interest, automatically replacing the anatomical plane schematic corresponding to the anatomical plane of interest with the ultrasonic image thumbnail, and causing the display to display the same.

Provided in some embodiments of the present application is an ultrasonic imaging system, comprising: a probe, configured to send or receive an ultrasonic signal; a processor; and a display, configured to receive an instruction from the processor so as to perform display. The processor is configured to: generate a plurality of anatomical plane schematics, and cause a display to display the same, each one of the plurality of anatomical plane schematics respectively corresponding to a different anatomical plane of interest; acquire an ultrasonic image of the anatomical plane of interest; and automatically generate an ultrasonic image thumbnail of the anatomical plane of interest, automatically replace the anatomical plane schematic corresponding to the anatomical plane of interest with the ultrasonic image thumbnail, and cause the display to display the same.

Provided in some embodiments of the present application is a non-transitory computer-readable medium, storing a computer program having at least one code segment executable by a machine to cause the machine to perform the following steps: generating a plurality of anatomical plane schematics, and causing a display to display the same, each one of the plurality of anatomical plane schematics respectively corresponding to a different anatomical plane of interest; acquiring an ultrasonic image of the anatomical plane of interest; and automatically generating an ultrasonic image thumbnail of the anatomical plane of interest, automatically replacing the anatomical plane schematic corresponding to the anatomical plane of interest with the ultrasonic image thumbnail, and causing the display to display the same.

It should be understood that the brief description above is provided to introduce, in simplified form, some concepts that will be further described in the detailed description. The brief description above is not meant to identify key or essential features of the claimed subject matter. The scope is defined uniquely by the claims that follow the detailed description. Furthermore, the claimed subject matter is not limited to implementations that solve any disadvantages noted above or in any section of the present disclosure.

BRIEF DESCRIPTION OF THE DRAWINGS

The present application will be better understood by reading the following description of non-limiting embodiments with reference to the accompanying drawings, where.

DETAILED DESCRIPTION

Specific implementations of the present invention will be described in the following. It should be noted that during the specific description of the implementations, it is impossible to describe all features of the actual implementations in detail in present invention for the sake of brief description. It should be understood that in the actual implementation process of any implementations, just as in the process of any engineering project or design project, a variety of specific decisions are often made to achieve specific goals of the developer and to meet system-related or business-related constraints, which may also vary from one implementation to another. Furthermore, it should also be understood that although efforts made in such development processes may be complex and tedious, for those of ordinary skill in the art related to the content disclosed in the present invention, some design, manufacture, or production changes based on the technical content disclosed in the present disclosure are only common technical means, and should not be construed as insufficient content of the present disclosure.

Unless otherwise defined, the technical or scientific terms used in the claims and the description are as they are usually understood by those of ordinary skill in the art to which the present invention pertains. "First", "second" and similar words used in the present invention and the claims do not denote any order, quantity or importance, but are merely intended to distinguish between different constituents. The terms "one" or "a/an" and similar terms do not denote a limitation of quantity, but rather the presence of at least one. The terms "include" or "comprise" and similar terms mean that an element or article preceding the term "include" or "comprise" encompasses elements or articles and their equivalent elements listed after "include" or "comprise," and does not exclude other elements or articles. The terms "connect" or "connected" and similar words are not limited to physical or mechanical connections, and are not limited to direct or indirect connections.

Figure 1:
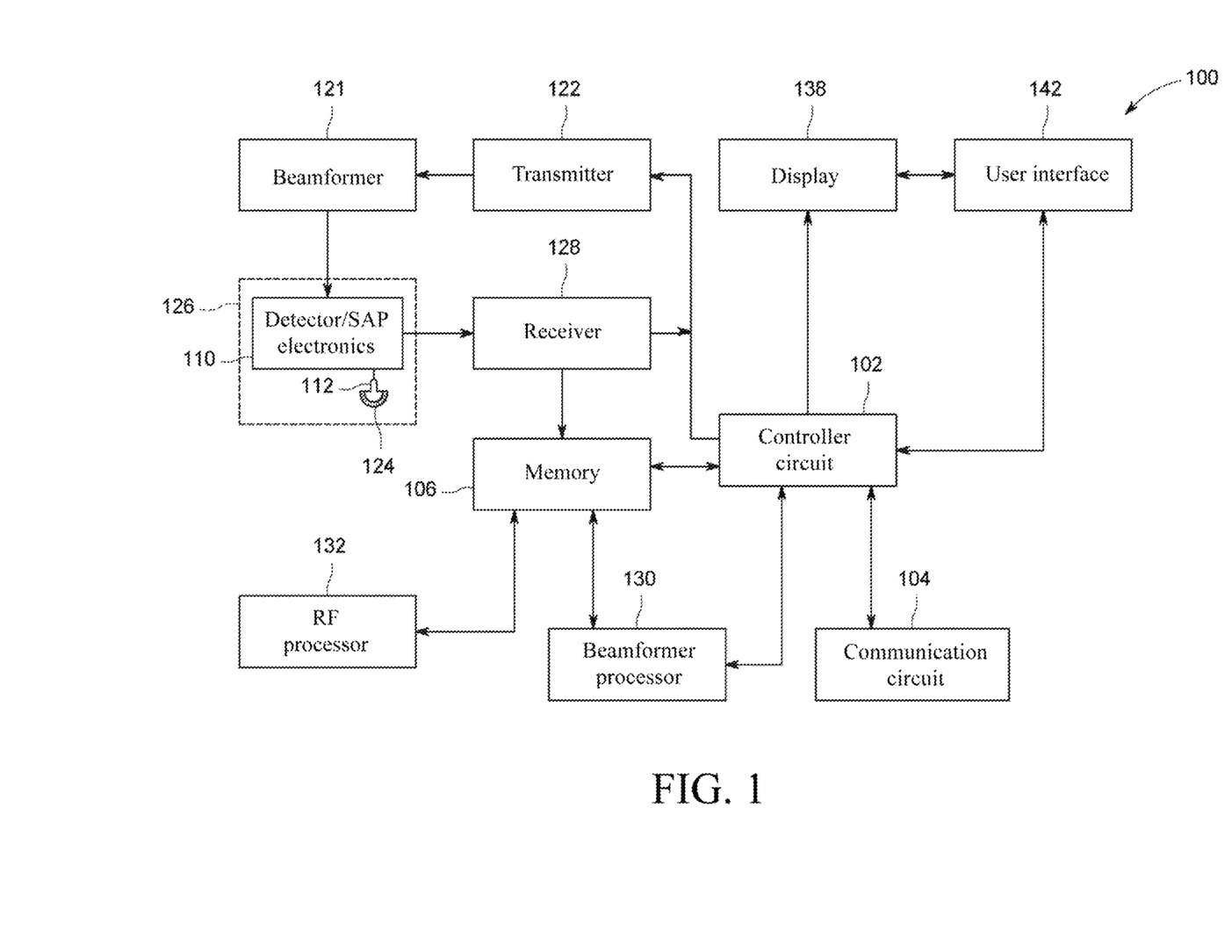
FIG. 1 is a schematic diagram of an ultrasonic imaging system according to some embodiments of the present application.

FIG. 1 shows a schematic block diagram of an embodiment of an ultrasonic imaging system 100. The ultrasonic imaging system 100 may include a controller circuit 102, a display 138, a user interface 142, a probe 126, and a memory 106 operatively connected to a communication circuit 104.

The controller circuit 102 is configured to control operation of the ultrasonic imaging system 100. The controller circuit 102 may include one or more processors. Optionally, the controller circuit 102 may include a central processing unit (CPU), one or more microprocessors, a graphics processing unit (GPU), or any other electronic assembly capable of processing inputted data according to a specific logic instruction. Optionally, the controller circuit 102 may include and/or represent one or more hardware circuits or circuitry including, connected to, or including and connected to one or more processors, controllers, and/or other hardware logic-based devices. Additionally or alternatively, the controller circuit 102 may execute instructions stored on a tangible and non-transitory computer-readable medium (e.g., the memory 106).

The controller circuit 102 may be operatively connected to and/or control the communication circuit 104. The communication circuit 104 is configured to receive and/or transmit information along a bidirectional communication link with one or more optional ultrasonic imaging systems, remote servers, etc. The remote server may represent and include patient information, a machine learning algorithm, a remotely stored medical image from a previous scan and/or diagnosis and treatment period of a patient, etc. The communication circuit 104 may represent hardware for transmitting and/or receiving data along a bidirectional communication link. The communication circuit 104 may include a transceiver, a receiver, a transceiver, etc., and associated circuitry (e.g., an antenna) for communicating (e.g., transmitting and/or receiving) in a wired and/or wireless manner with the one or more optional ultrasonic imaging systems, remote servers, etc. For example, protocol firmware for transmitting and/or receiving data along a bidirectional communication link may be stored in the memory 106 accessed by the controller circuit 102. The protocol firmware provides network protocol syntax to the controller circuit 102 so as to assemble a data packet, establish and/or segment data received along the bidirectional communication link, and so on.

The bidirectional communication link may be a wired (e.g., via a physical conductor) and/or wireless communication (e.g., via radio frequency (RF)) link for exchanging data (e.g., a data packet) between the one or more optional ultrasonic imaging systems, remote servers, etc. The bidirectional communication link may be based on standard communication protocols, such as Ethernet, TCP/IP, WiFi, 802.11, a customized communication protocol, Bluetooth, etc.

The controller circuit 102 is operatively connected to the display 138 and the user interface 142. The display 138 may include one or more liquid crystal displays (e.g., light emitting diode (LED) backlights), organic light emitting diode (OLED) displays, plasma displays, CRT displays, and the like. The display 138 may display patient information, one or more medical images and/or videos, a graphical user interface, or a component received by the display 138 from the controller circuit 102, one or more 2D, 3D or 4D ultrasonic image data sets from ultrasonic data stored in the memory 106, or anatomical measurement, diagnosis, processing information, etc. currently acquired in real time.

The user interface 142 controls operation of the controller circuit 102 and the ultrasonic imaging system 100. The user interface 142 is configured to receive input from a clinician and/or an operator of the ultrasonic imaging system 100. The user interface 142 may include a keyboard, a mouse, a touch pad, one or more physical buttons, and the like. Optionally, the display 138 may be a touch screen display that includes at least a portion of the user interface 142. For example, a portion of the user interface 142 may correspond to a graphical user interface (GUI) generated by the controller circuit 102 and shown on the display 138. The touch screen display may detect presence of a touch from the operator on the display 138, and may also identify the position of the touch relative to a surface area of the display 138. For example, a user may select, by touching or contacting the display 138, one or more user interface components of the user interface (GUI) shown on the display. User interface components may correspond to icons, text boxes, menu bars, etc. shown on the display 138. A clinician may select, control, and use a user interface component, interact with the same, and so on so as to send an instruction to the controller circuit 102 to perform one or more operations described in the present application. For example, the touch can be applied by using at least one of a hand, a glove, a stylus, and the like.

The memory 106 may include a parameter, an algorithm, one or more ultrasonic examination protocols, a data value, and the like used by the controller circuit 102 to perform one or more operations described in the present application. The memory 106 may be a tangible and non-transitory computer-readable medium such as a flash memory, a RAM, a ROM, an EEPROM, etc. The memory 106 may include a set of learning algorithms (e.g., a convolutional neural network algorithm, a deep learning algorithm, a decision tree learning algorithm, etc.) configured to define an image analysis algorithm. During execution of the image analysis algorithm, the controller circuit 102 is configured to identify an anatomical plane of interest of an anatomical structure of interest in a medical image. Optionally, an image analysis algorithm may be received by means of the communication circuit 104 along one of bidirectional communication links, and stored in the memory 106.

The image analysis algorithm may be defined by one or more algorithms to identify fields of view of the anatomical structure of interest on the basis of one or more anatomical markers within the medical image (e.g., a boundary, a thickness, a pixel value change, a valve, a cavity, a chamber, an edge or inner layer, a vessel structure, etc.), a modality or pattern of the medical image (e.g., color blood flow), etc. The one or more anatomical markers may represent features of pixels and/or volume elements of the medical image, such as a histogram of oriented gradients, point features, covariance features, binary mode features, and the like. For example, anatomical markers may represent anatomical features and/or structures of anatomical structures of interest, fiducial markers, and the like. For example, the image analysis algorithm may be defined by using prediction of object identification within the medical image by using one or more deep neural networks.

The image analysis algorithm may correspond to an artificial neural network formed by the controller circuit 102 and/or the remote server. The image analysis algorithm may be divided into two or more layers, such as an input layer for receiving an input image, an output layer for outputting an output image, and/or one or more intermediate layers. Layers of a neural network represent different groups or sets of artificial neurons, and may represent different functions that are executed by the controller circuit 102 with respect to an input image (e.g., a medical image acquired and/or generated by the ultrasonic imaging system 100) to identify an object of the input image and determine an anatomical plane of interest of an anatomical structure of interest shown in the input image. The artificial neurons in the layer of the neural network may examine individual pixels in the input image. The artificial neurons use different weights in a function applied to the input image, so as to attempt to identify an object in the input image. The neural network produces an output image by assigning or associating different pixels in the output image with different anatomical markers on the basis of analysis of pixel characteristics.

The image analysis algorithm is defined by a plurality of training images, and the plurality of training images may be grouped into different anatomical planes of interest of the anatomical structure of interest. The training image may represent different orientations and/or cross sections of the anatomical structure of interest corresponding to different fields of view. Additionally or alternatively, the image analysis algorithm may be defined by the controller circuit on the basis of a classification model. The classification model may correspond to a machine learning algorithm based on a classifier (e.g., a random forest classifier, principal component analysis, etc.) configured to identify and/or assign anatomical markers to multiple identities or categories on the basis of an overall shape, a spatial position relative to the anatomical structure of interest, intensity, etc.

The controller circuit 102 executing an image analysis algorithm (e.g., an image analysis algorithm) may determine the anatomical structure of interest on the basis of a relationship of the anatomical markers relative to each other, modality, etc. The relationship may include orientations of the anatomical markers relative to each other. For example, the orientation of the anatomical marker based on the cavity representing the anatomical structure of interest may be used by the controller circuit 102 to identify the anatomical plane of interest.

Additionally or alternatively, the controller circuit 102 may define a separate image analysis algorithm customized and/or configured for different selected anatomical structures of interest. For example, multiple image analysis algorithms may be stored in the memory 106. Each one of the plurality of image analysis algorithms may be customized and/or configured on the basis of different training images (e.g., a set of input images) to configure layers of different neural networks, so as to select anatomical structures of interest, classification models, supervised learning models, and the like. On the basis of a protocol selected and/or defined by a clinician, the controller circuit 102 may select an image analysis algorithm of the anatomical structure of interest corresponding to the protocol in the plurality of image analysis algorithms.

It can be noted that a machine learning algorithm used to define an image analysis algorithm is a schematic embodiment, and a person skilled in the art may use other methods.

With continued reference to FIG. 1, the ultrasonic imaging system 100 may include the probe 126, and the probe 126 has a transmitter 122, a transmission beamformer 121, and a detector/SAP electronics 110. The detector/SAP electronics 110 may be used to control switching of transducer elements 124. The detector/SAP electronics 110 may also be used to group the transducer elements 124 into one or more sub-holes.

The probe 126 may be configured to acquire ultrasonic data or information from an anatomical structure of interest (e.g., organs, blood vessels, heart, bones, etc.) of a patient. The probe 126 is communicatively connected to the controller circuit 102 by means of the transmitter 122. The transmitter 122 transmits a signal to the transmission beamformer 121 on the basis of acquisition settings received by the controller circuit 102. The acquisition settings may define the amplitude, pulse width, frequency, gain setting, scanning angle, power, time gain compensation (TGC), resolution, and the like of ultrasonic pulses emitted by the transducer element 124. The transducer element 124 emits a pulsed ultrasonic signal into a patient (e.g., the body). The acquisition settings may be defined by a user operating the user interface 142. The signal transmitted by the transmitter 122, in turn, drives a plurality of transducer elements 124 within a transducer array 112.

The transducer element 124 transmits a pulsed ultrasonic signal to a body (e.g., a patient) or a volume that corresponds to an acquisition setting along one or more scanning planes. The ultrasonic signal may include, for example, one or more reference pulses, one or more push pulses (e.g., shear waves), and/or one or more pulsed wave Doppler pulses. At least a portion of the pulsed ultrasonic signal is backscattered from the anatomical structure of interest (e.g., the organ, bone, heart, breast tissue, liver tissue, cardiac tissue, prostate tissue, newborn brain, embryo, abdomen, etc.) to produce echoes. Depending on the depth or movement, echoes are delayed in time and/or frequency, and received by the transducer elements 124 within the transducer array 112. The ultrasonic signal may be used for imaging, for producing and/or tracking the shear wave, for measuring changes in position or velocity within the anatomical structure, the compressive displacement difference (e.g., strain) of the tissue, and/or for treatment and other applications. For example, the probe 126 may deliver low energy pulses during imaging and tracking, deliver medium and high energy pulses to produce shear waves, and deliver high energy pulses during treatment.

The transducer element 124 converts a received echo signal into an electrical signal that can be received by a receiver 128. The receiver 128 may include one or more amplifiers, analog/digital converters (ADCs), and the like. The receiver 128 may be configured to amplify the received echo signal after appropriate gain compensation, and convert these analog signals received from each transducer element 124 into a digitized signal that is temporally uniformly sampled. The digitized signals representing the received echoes are temporarily stored in the memory 106. The digitized signals correspond to backscattered waves received by each transducer element 124 at different times. After being digitized, the signal may still retain the amplitude, frequency, and phase information of the backscattered wave.

Optionally, the controller circuit 102 may retrieve a digitized signal stored in the memory 106 for use in a beamformer processor 130. For example, the controller circuit 102 may convert the digitized signal into a baseband signal or compress the digitized signal.

The beamformer processor 130 may include one or more processors. If desired, the beamformer processor 130 may include a central processing unit (CPU), one or more microprocessors, or any other electronic assembly capable of processing inputted data according to specific logic instructions. Additionally or alternatively, the beamformer processor 130 may execute instructions stored on a tangible and non-transitory computer-readable medium (e.g., the memory 106) to perform beamforming computation by using any suitable beamforming method, such as adaptive beamforming, synthetic emission focusing, aberration correction, synthetic aperture, clutter suppression, and/or adaptive noise control, among others. If desired, the beamformer processor 130 may be integrated with and/or part of the controller circuit 102. For example, operations described as being performed by the beamformer processor 130 may be configured to be performed by the controller circuit 102.

The beamformer processor 130 performs beamforming on the digitized signal of the transducer element, and outputs a radio frequency (RF) signal. The RF signal is then provided to an RF processor 132 for processing the RF signal. The RF processor 132 may include one or more processors. If desired, the RF processor 132 may include a central processing unit (CPU), one or more microprocessors, or any other electronic assembly capable of processing inputted data according to specific logic instructions. Additionally or alternatively, the RF processor 132 may execute instructions stored on a tangible and non-transitory computer-readable medium (e.g., the memory 106). If desired, the RF processor 132 may be integrated with and/or part of the controller circuit 102. For example, operations described as being performed by the RF processor 132 may be configured to be performed by the controller circuit 102.

The RF processor 132 may generate, for a plurality of scanning planes or different scanning modes, different ultrasonic image data types and/or modes, e.g., B-mode, color Doppler (e.g., color blood flow, velocity/power/variance), tissue Doppler (velocity), and Doppler energy, on the basis of a predetermined setting of a first model. For example, the RF processor 132 may generate tissue Doppler data for the multiple scanning planes. The RF processor 132 acquires information (e.g., I/Q, B-mode, color Doppler, tissue Doppler, and Doppler energy information) related to multiple data pieces, and stores data information in the memory 106. The data information may include time stamp and orientation/rotation information.

Optionally, the RF processor 132 may include a composite demodulator (not shown) for demodulating an RF signal to generate an IQ data pair representing an echo signal. The RF or IQ signal data may then be provided directly to the memory 106 so as to be stored (e.g., stored temporarily). As desired, output of the beamformer processor 130 may be communicated directly to the controller circuit 102.

The controller circuit 102 may be configured to process acquired ultrasonic data (e.g., RF signal data or an IQ data pair), and prepare and/or generate an ultrasonic image data frame representing the anatomical structure of interest so as to display the same on the display 138. The acquired ultrasonic data may be processed by the controller circuit 102 in real time when an echo signal is received in a scanning or treatment process of ultrasonic examination. Additionally or alternatively, the ultrasonic data may be temporarily stored in the memory 106 in a scanning process, and processed in a less real-time manner in live or offline operations.

The memory 106 may be used to store processed frames of acquired ultrasonic data that are not scheduled to be immediately displayed, or may be used to store post-processed images (e.g., shear wave images, and strain images), firmware or software corresponding to, e.g., a graphical user interface, one or more default image display settings, programmed instructions, and the like. The memory 106 may store a medical image, such as a 3D ultrasonic image data set of ultrasonic data, where such a 3D ultrasonic image data set is accessed to present 2D and 3D images. For example, a 3D ultrasonic image data set may be mapped to the corresponding memory 106 and one or more reference planes. Processing of ultrasonic data that includes the ultrasonic image data set may be based in part on user input, e.g., a user selection received at the user interface 142.

Figure 2:
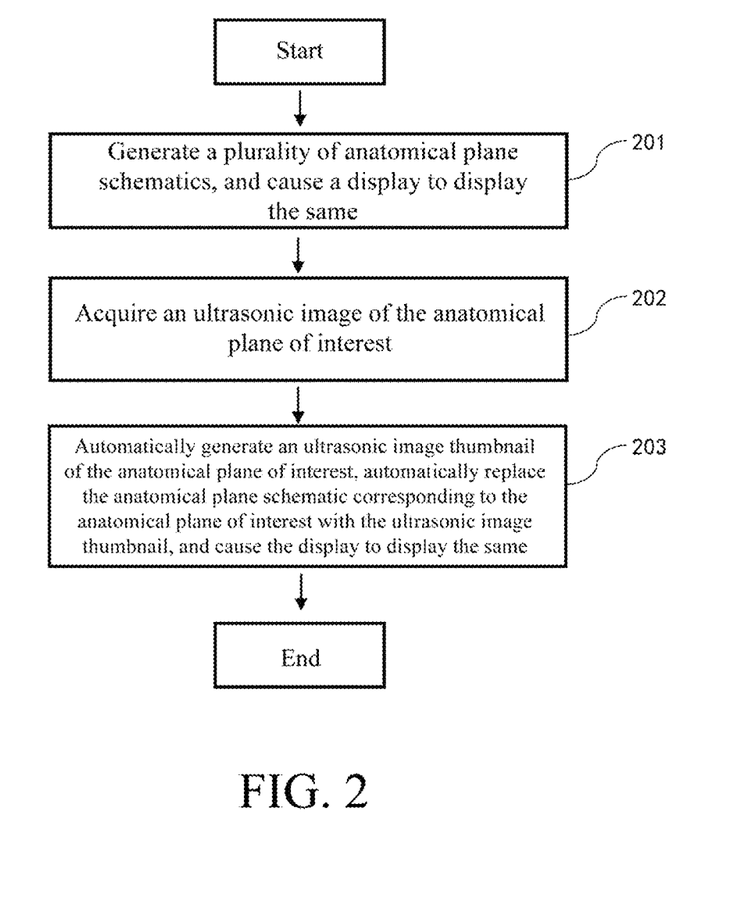
FIG. 2 is a flowchart of an ultrasonic imaging method according to some embodiments of the present application.

Referring to FIG. 2, FIG. 2 shows a flowchart of an ultrasonic imaging method 200 according to some embodiments of the present invention.

In step 201, generating a plurality of anatomical plane schematics, and causing a display to display the same, each one of the plurality of anatomical plane schematics respectively corresponding to a different anatomical plane of interest.

This step may be implemented by at least a portion of the controller circuit 102. For example, this step may be implemented by the processor on the basis of an instruction of a user. The user may determine, according to an ultrasonic scanning requirement, an anatomical plane of which an ultrasonic image needs to be acquired, i.e., an anatomical plane of interest. The controller circuit 102 generates, according to anatomical planes of interest, a plurality of anatomical plane schematics in a one-to-one correspondence with the same.

A variety of methods may be used to determine the anatomical plane of interest. In some embodiments, the anatomical plane of interest may correspond to an ultrasonic scanning protocol prestored in the memory 106. For example, the memory 106 may prestore standard anatomical planes of different organs (e.g., heart, kidney, lung, liver, bladder, brain, fetus, newborn brain, embryo, abdomen, etc.), vascular structures (e.g., veins), and tissue (e.g., breast tissue, liver tissue, cardiac tissue, prostate tissue, etc.) to be scanned. The set of these standard anatomical planes can be selected by the user as an ultrasonic scanning protocol. Once the user selects an ultrasonic scanning protocol for a certain location to be scanned, the controller circuit 102 can generate a plurality of anatomical plane schematics corresponding to the ultrasonic scanning protocol, and cause the display to display the same. In an alternative embodiment, the plurality of anatomical plane schematics described above may be customized by the user according to an actual scanning requirement. For example, the user may select, by means of the user interface 142, an anatomical plane of which an ultrasonic image needs to be acquired. The anatomical plane autonomously selected by the user is used as the anatomical plane of interest. The controller circuit 102 generates, according to the above selection of the user, anatomical plane schematics in a one-to-one correspondence with the anatomical planes of interest.

In step 202, acquiring an ultrasonic image of the anatomical plane of interest.

This step may be implemented by at least a portion of the controller circuit 102. An ultrasonic echo signal received by the probe 126 from a location to be scanned is processed by the controller circuit 102, so as to acquire an ultrasonic image of a current position. An updated ultrasonic image can be acquired by adjusting relative positions of the probe 126 and the location to be scanned. Via the above adjustment, the controller circuit 102 can acquire the ultrasonic image of the anatomical plane of interest. A variety of methods may be used to determine that an acquired ultrasonic image is an ultrasonic image of the anatomical plane of interest. In some embodiments, this may be implemented by means of determination performed by the user. For example, the user may observe a current ultrasonic image displayed in real time on the display 138, and determine, according to an anatomical marker reflected on the ultrasonic image, whether the current ultrasonic image is an ultrasonic image of the anatomical plane of interest. In some other embodiments, the controller circuit 102 may perform determination automatically. Exemplary description of automatic determination performed by the controller circuit 102 is provided below.

In step 203, automatically generating an ultrasonic image thumbnail of the anatomical plane of interest, automatically replacing the anatomical plane schematic corresponding to the anatomical plane of interest with the ultrasonic image thumbnail, and causing the display to display the same.

This step may be implemented by at least a portion of the controller circuit 102. The ultrasonic image of the anatomical plane of interest acquired in step 202 may be processed to generate an ultrasonic image thumbnail. In a non-limiting embodiment, the processor may generate a corresponding ultrasonic image thumbnail by reducing the resolution and/or size of the ultrasonic image described above. It will be appreciated that an ultrasonic image thumbnail generated by performing processing has image features, especially a feature of a key anatomical position, similar to those of a corresponding ultrasonic image, and has a smaller size. The above process may be performed automatically. For example, a corresponding ultrasonic image thumbnail may be automatically generated after the ultrasonic image of the anatomical plane of interest is determined in step 202. Automatic generation of ultrasonic image thumbnails can reduce steps to be performed by the user. After the ultrasonic image thumbnail is generated, the anatomical plane schematic corresponding to the anatomical plane of interest is automatically replaced with the ultrasonic image thumbnail, and the display is caused to display the same. A replacement process may also be automatically performed by the processor. On the graphical user interface of the display, the user can intuitively see that an anatomical plane schematic previously used to represent an anatomical plane of interest is replaced with a thumbnail of an ultrasonic image of the anatomical plane of interest.

The method of the above embodiment enables the user to intuitively see an anatomical structure of a specific anatomical plane of interest when the user needs to scan a plurality of anatomical planes of interest (e.g., standard anatomical planes meeting requirements of the ultrasonic scanning protocol). Specifically, an anatomical plane schematic can provide the user with an intuitive, easy-to-understand prompt for an anatomical plane of interest represented by the anatomical plane schematic. In addition, in a scanning process, after an ultrasonic image of a certain anatomical plane of interest is acquired, an anatomical plane schematic corresponding to the anatomical plane of interest is automatically replaced with a thumbnail of the ultrasonic image, so that the user can visually obviously distinguish between an anatomical structure of interest of which an ultrasonic image has been acquired and an anatomical structure of interest of which no ultrasonic image has been acquired, thereby facilitating improvement of scanning efficiency.

Figure 3:
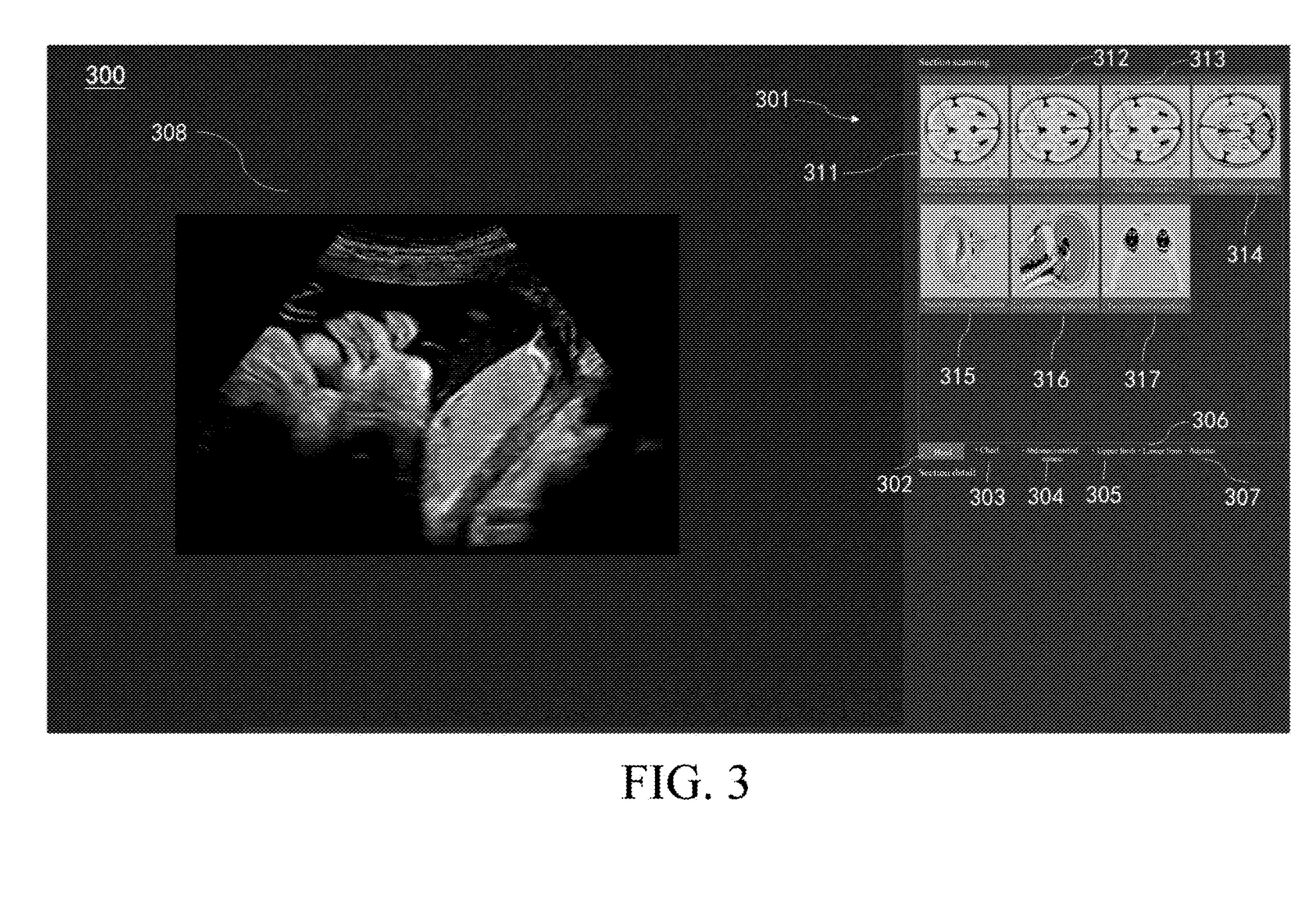
FIG. 3 is a schematic diagram of a graphical user interface of a display in some embodiments of the present application.

The steps of the above embodiments are described in further detail below. Referring to FIG. 3, FIG. 3 is a schematic diagram of a graphical user interface 300 of a display in some embodiments of the present application.

As shown in FIG. 3, the graphical user interface 300 includes a plurality of anatomical plane schematics 301. A method for generating the anatomical plane schematic 301 may be as that shown in step 201 described above, and the anatomical plane schematic 301 is generated by the processor of the controller circuit 102 on the basis of an instruction of a user. For example, an ultrasonic scanning protocol prestored in the memory 106 may be generated by means of autonomous selection performed by the user. For example, FIG. 3 shows a non-limiting embodiment of a fetus scanning protocol. Once the user selects the scanning protocol, the user interface 300 generates a plurality of anatomical plane schematics 301 corresponding to standard anatomical planes of the fetus scanning protocol.

In a non-limiting embodiment, the anatomical plane schematics 301 may include a biparietal diameter schematic 311, a lateral ventricle section schematic 312, a cavity of septum pellucidum section schematic 313, a cerebellum cross-section schematic 314, a nasolabial coronal section schematic 315, a lower-mid face sagittal section schematic 316, and a two-eye socket section schematic 317. The above anatomical plane schematics may be classified into a first anatomical plane schematic set 302 (e.g., a head anatomical plane schematic set). Similarly, a plurality of anatomical plane schematic sets 303, 304, 305, 306, and 307 may also be included. The plurality of anatomical plane schematic sets may respectively include different anatomical plane schematics (not fully shown in the drawings). Such a configuration manner enables the limited user interface 300 to accommodate sufficient anatomical plane schematics. Further, each anatomical plane schematic set may include anatomical plane schematics associated with each other with respect to the physiological structure, so that a scanning operator can be easily guided to perform scanning in a regular scanning order, thereby avoiding omission. For example, the first anatomical plane schematic set 302 corresponding to the standard anatomical planes of the fetus scanning protocol shown in FIG. 3 may be configured to correspond to a fetal head scanning protocol. Accordingly, a second anatomical plane schematic set 303 may be configured to correspond to a fetal chest scanning protocol. A third anatomical plane schematic set 304 may be configured to correspond to a fetal abdomen/vertebral column scanning protocol. A fourth anatomical plane schematic set 305 may be configured to correspond to a fetal upper limb scanning protocol. A fifth anatomical plane schematic set 306 may be configured to correspond to a fetal lower limb scanning protocol. A sixth anatomical plane schematic set 307 may be configured to correspond to a fetal adjunct scanning protocol. In such a configuration manner, the large number of miscellaneous standard anatomical planes that need to be scanned are classified regularly, thereby facilitating improvement of scanning efficiency of a scanning operator.

Further, the anatomical plane schematic is configured to be a graphical display of the corresponding anatomical plane of interest. Referring to FIG. 3, the anatomical plane schematics 311-317 in the plurality of anatomical plane schematics 301 are respectively configured to be graphical displays of respective corresponding anatomical planes of interest. It will be appreciated that the graphical display refers to a graphic similar to a key shape and structure of an anatomical plane of interest. For example, the two-eye socket section schematic 317 in FIG. 3 clearly shows structural features, including the eyes, of the corresponding anatomical plane of interest thereof (a two-eye socket section). Compared with a pure text representation or other representation manners, such a configuration manner can more intuitively and efficiently indicate an anatomical plane of interest that needs to be scanned to a scanning operator, so that the scanning operator can easily adjust the position of the probe to quickly acquire an ultrasonic image of the required anatomical plane of interest.

With continued reference to FIG. 3, the graphical user interface 300 also includes an ultrasonic image 308 generated in real time. Regarding a method of generating the real-time ultrasonic image 308, reference can be made to step 202 described above. For example, an ultrasonic echo signal received by the probe 126 from a location to be scanned is processed by the controller circuit 102, so as to acquire a real-time ultrasonic image of a current position.

Further, at least one anatomical marker of the real-time ultrasonic image can be automatically identified, and it is determined, on the basis of the at least one anatomical marker, that the real-time ultrasonic image is an ultrasonic image of the anatomical plane of interest. An anatomical marker identification and analysis method is as described in any embodiment described above, and details will not be described herein again. As shown in FIG. 3, after the processor of the controller circuit 102 performs automatic identification on the real-time ultrasonic image 308, if no anatomical marker therein is identified, then the processor determines accordingly that the current real-time ultrasonic image is not an ultrasonic image of the anatomical plane of interest, and does not perform the next operation. In this case, the scanning operator needs to adjust the position of the probe until an ultrasonic image of the anatomical plane of interest is acquired. Subsequent processes for acquiring ultrasonic images of anatomical planes of interest are described in detail below.

Figure 4:
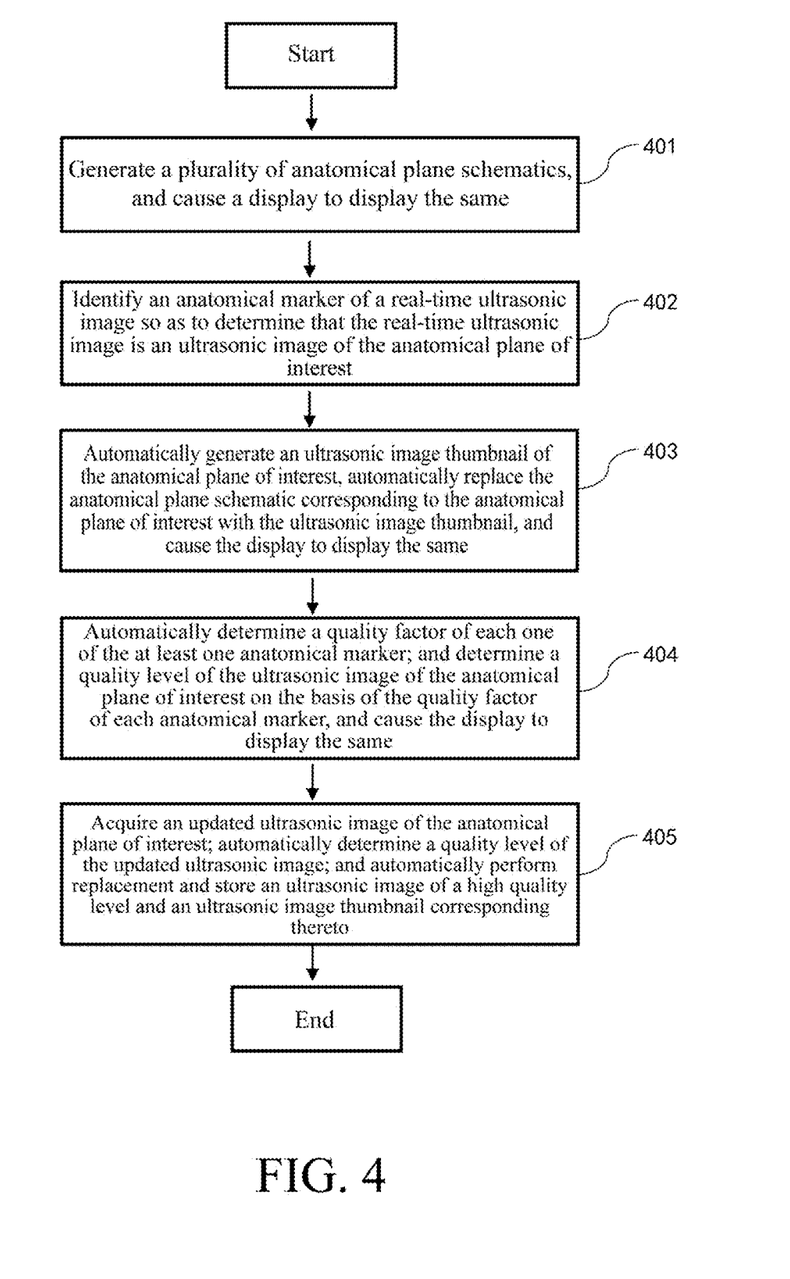
FIG. 4 is a schematic diagram of an ultrasonic imaging method according to some other embodiments of the present application.

Referring to FIG. 4, FIG. 4 shows a schematic diagram of an ultrasonic imaging method 400 according to some other embodiments of the present application.

In step 401, generating a plurality of anatomical plane schematics, and causing a display to display the same. Each one of the plurality of anatomical plane schematics respectively corresponds to a different anatomical plane of interest. This step can be implemented with reference to step 201 or the implementation described in any embodiment described above, and details will not be described herein again.

In step 402, identifying an anatomical marker of a real-time ultrasonic image so as to determine that the real-time ultrasonic image is an ultrasonic image of the anatomical plane of interest. Specifically, the real-time ultrasonic image may be generated on the basis of an ultrasonic signal received by the probe. Further, at least one anatomical marker of the real-time ultrasonic image is automatically identified, and it is determined, on the basis of the at least one anatomical marker, that the real-time ultrasonic image is an ultrasonic image of the anatomical plane of interest.

Figure 5:
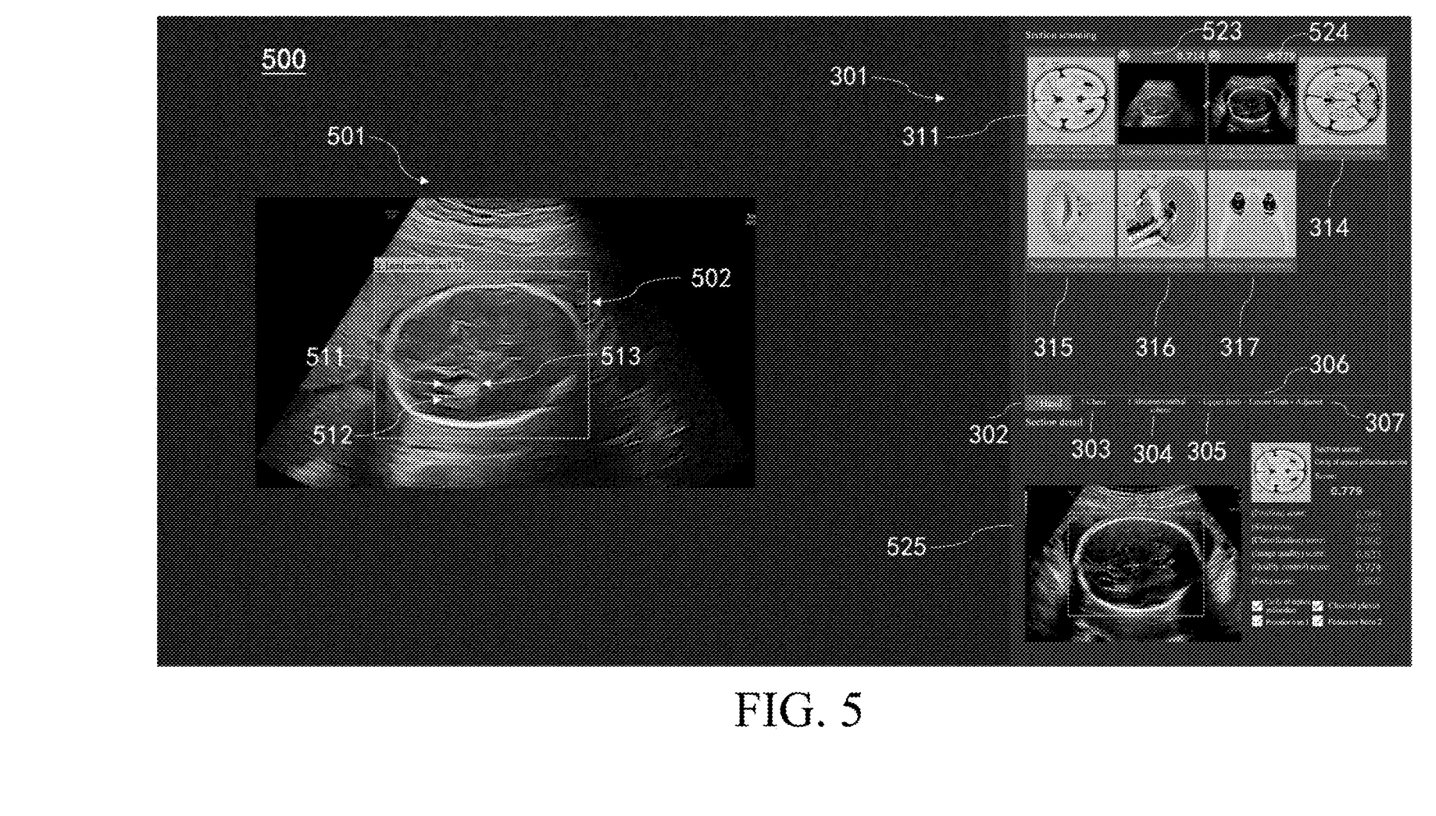
FIG. 5 is a schematic diagram of a graphical user interface of a display in some other embodiments of the present application.

Regarding the identification and determination of the real-time ultrasonic image described above, reference may be made to FIG. 5. FIG. 5 is a schematic diagram of a graphical user interface 500 of a display in some other embodiments of the present application. This graphical user interface 500 shows an example of a user acquiring an ultrasonic image of an anatomical plane of interest.

The graphical user interface 500 includes a plurality of anatomical plane schematics 301. A specific configuration manner of the anatomical plane schematic 301 described above can be as described in FIG. 3 and the corresponding embodiments thereof, and details will not be described herein again. The graphical user interface 500 also shows generating a real-time ultrasonic image 501 on the basis of an ultrasonic signal received by the probe. The real-time ultrasonic image 501 includes at least one anatomical marker 511, 512, 513. On the basis that the above at least one includes at least one anatomical marker 511, 512, 513, the real-time ultrasonic image 501 is identified as an ultrasonic image of the anatomical plane of interest. In a non-limiting embodiment, the anatomical marker 511 represents a posterior horn 1. The anatomical marker 512 represents a posterior horn 2. The anatomical marker 513 represents choroid plexus. On the basis of the anatomical markers described above, the processor can identify the real-time ultrasonic image 501 as an ultrasonic image of the anatomical plane of interest, i.e., a lateral ventricle section. In an embodiment, each one of the anatomical markers described above is displayed on the real-time ultrasonic image 501. It will be appreciated that in an alternative embodiment, the anatomical markers described above may not be displayed. In addition, although FIG. 5 shows that the anatomical plane of interest is a lateral ventricle section, the anatomical plane may be other one depending on an image identification result, and correspondingly, anatomical markers corresponding to different anatomical planes of interest may also be different. Details will not be described herein again.

In such a configuration manner, a scanning operator does not need to perform determination on an anatomical plane by means of only the naked eyes, and a machine automatically provides an identification result, and informs the same to the scanning operator, thereby improving the scanning efficiency.

In step 403, automatically generating an ultrasonic image thumbnail of the anatomical plane of interest, automatically replacing the anatomical plane schematic corresponding to the anatomical plane of interest with the ultrasonic image thumbnail, and causing the display to display the same.

With continued reference to FIG. 5, detailed description is provided below. As shown in FIG. 5, after it is determined that the real-time ultrasonic image 501 is an ultrasonic image of the anatomical plane of interest (e.g., a lateral ventricle section), an ultrasonic image thumbnail 523 of the anatomical plane of interest is automatically generated. A method for generating a thumbnail may be processing the real-time ultrasonic image 501, for example, reducing the resolution and/or dimensions, so that the dimensions and/or size thereof is adjusted to be adapted to a corresponding anatomical plane schematic of the anatomical plane of interest, e.g., the lateral ventricle section schematic 313 shown in FIG. 3. Such a thumbnail, while maintaining the appearance consistent with that of the ultrasonic image 501, can have a smaller size so as to be easily displayed as a label. Further, the above-described anatomical plane schematic corresponding to the anatomical plane of interest is automatically replaced with the ultrasonic image thumbnail 523 that is displayed.

In such a configuration manner, the scanning operator can intuitively see, from the change in the area of the ultrasonic image thumbnail 301 described above, the ultrasonic image of the anatomical plane of interest that has been acquired on the basis of the current scanning protocol and the ultrasonic image of the anatomical plane of interest that has not been acquired, thereby facilitating adjustment made to the probe to perform next ultrasonic scanning.

In step 404, automatically determining a quality factor of each one of the at least one anatomical marker; and determining a quality level of the ultrasonic image of the anatomical plane of interest on the basis of the quality factor of each anatomical marker, and causing the display to display the same.

Such a configuration manner allows the scanning operator to easily and intuitively determine how to adjust the probe to acquire a high quality ultrasonic image. Referring to FIG. 5, a quality factor of each one of the at least one anatomical marker 511, 512, 513 is determined automatically. A method of determination may be any method in the art. For example, in an example, the determination of the quality factor is performed automatically by using an artificial intelligence model. A model training method may be similar to the example described above. In another example, other methods may also be employed, for example, a quality factor determination algorithm model is used. Details will not be described herein again. Further, the quality factor of each anatomical marker described above can be used to determine a quality level of the ultrasonic image 501 of the anatomical plane of interest, and display is performed.

A method for presenting the quality level may be arbitrary. In an example, the ultrasonic image 501 of the anatomical plane of interest may be configured to include a visual display of the quality level described above. In another example, the ultrasonic image thumbnail 523 may be configured to include a visual display of the quality level described above. In other implementations, both the ultrasonic image 501 and the ultrasonic image thumbnail 523 may be caused to include the visual display of the quality level. Exemplary description of a specific configuration manner of the visual display is provided below. It should be noted that in the teachings of the present disclosure, these configuration manners may be freely selected/combined/replaced.

In an example, as shown in FIG. 5, presentation may be performed numerically. For example, by determining the quality factor of each one of the at least one anatomical marker 511, 512, 513, the quality level of the ultrasonic image 501 is calculated, and is 0.714. This number may be displayed in an appropriate position. For example, a frame 502 is generated around the ultrasonic image 501 of the anatomical plane of interest, and the number is display on an edge of the frame 502. Further, quality levels can also be represented by different colors. For example, green represents a relatively high quality level. Yellow represents a medium quality level. Red represents a relatively low quality level. The colors described above may be presented on the frame 502. For example, as shown in FIG. 5, the frame 502 in yellow represents the acceptable medium quality level. It will be appreciated that the color of the frame and the quality level represented thereby may be configured freely according to the teachings of the present disclosure, and details will not be described herein again.

In an example, the anatomical markers 511, 512, 513 are configured to be positioned in an anatomical position corresponding to the current ultrasonic image 501. The shape of the anatomical marker may be a spot as shown in FIG. 5 to ensure that the size thereof does not affect observation of the ultrasonic image 501 performed by the scanning operator. Alternatively, the anatomical marker may have other shapes. Further, the quality factor of each anatomical marker may be displayed visually. As shown in FIG. 5, a display method may be configuring anatomical markers to have different colors. The anatomical markers 511 and 513 have relatively large quality factors, and may be configured to be a green visual display. The anatomical marker 512 has a medium quality factor, and may be configured to be a yellow visual display. It will be appreciated that a color assignment rule may be a default rule in a memory, or may be customized by a user. In such a configuration manner, the visual displays of the quality levels described above include the visual display of the quality factor of each anatomical marker, so that the user can easily and quickly determine whether image quality is satisfactory and a major cause of unsatisfactory image quality.

In step 405, acquiring an updated ultrasonic image of the anatomical plane of interest; automatically determining a quality level of the updated ultrasonic image; and automatically performing replacement and storing an ultrasonic image of a high quality level and an ultrasonic image thumbnail corresponding thereto. It can be seen from the above description of the steps that the present application provides an intuitive indication to a scanning operator to monitor in real time whether an ultrasonic image of an anatomical plane of interest has been acquired, and enables the scanning operator to intuitively determine whether an acquired ultrasonic image is satisfactory. Further, in step 405, a method for updating a high quality ultrasonic image is provided to the scanning operator. For example, when the scanning operator finds that the quality level of the ultrasonic image 501 is not satisfactory, the scanning operator may adjust the probe. For example, an angle of the probe relative to the body surface, the position of the probe relative to the body surface, or a parameter of the probe, or the like may be adjusted. The quality factor of each one of the at least one anatomical marker 511, 512, 513 can provide a reference used by the scanning operator to adjust the probe. For example, for an anatomical marker having a small quality factor, the scanning operator may increase the quality factor in a targeted manner, thereby acquiring a high quality ultrasonic image. In embodiments of the present application, after the updated ultrasonic image of the anatomical plane of interest is acquired, and after the quality level of the updated ultrasonic image is automatically determined, replacement and storage of an ultrasonic image of a high level and a thumbnail thereof can be performed automatically, and the scanning operator does not need to perform any operation. For example, the scanning operator does not need to delete the low quality ultrasonic image acquired by means of previous scanning. In such a configuration manner, working efficiency of the scanning operator can be improved.

In addition to providing a user with the efficient and quick scanning solution for real-time scanning, further provided in some embodiments of the present application is a method for quickly viewing stored ultrasonic images. Detailed description is provided with reference to FIG. 5 and FIG. 6.

Referring first to FIG. 5, in addition to the ultrasonic image thumbnail 523 described above, another ultrasonic image thumbnail 524 may also be present in the area of the anatomical plane schematic 301. The ultrasonic image thumbnail 524 represents an ultrasonic image thumbnail of another anatomical plane of interest, and a method for generating the same will not be described herein again. In some embodiments, the ultrasonic images of these anatomical planes of interest and the ultrasonic image thumbnails are all automatically stored. Due to automatic identification and quality determination functions of the present application, the ultrasonic images and the ultrasonic image thumbnails described above can be automatically subjected to identification and determination. Correspondingly, a storage function can also be performed automatically, thereby reducing workload of the scanning operator. A location for the automatic storage may be the memory 106. The ultrasonic image thumbnail 524 and an ultrasonic image 601 of the anatomical plane of interest corresponding thereto (see FIG. 6) may be stored automatically in a scan prior to a current time point. In an example, after a complete scanning protocol is executed, the controller circuit checks the integrity of the scan automatically. When ultrasonic images of all anatomical planes of interest are acquired, the ultrasonic images are all stored again automatically. In the case that ultrasonic images of some anatomical planes of interest are missing, a notification is sent to prompt a user to perform storage manually. Such a configuration manner can notify the case that a scan is missing. In this manner, even the workload on the user is relatively heavy, the user does not miss any anatomical plane of interest that needs to be scanned.

In some embodiments, the processor may also be configured to, in response to a first instruction, zoom in and display the ultrasonic image thumbnail of the anatomical plane of interest described above (e.g., the ultrasonic image thumbnail 524). The ultrasonic image thumbnail 524 that is zoomed in and displayed may be as shown in a thumbnail zooming-in region 525 of FIG. 5. The thumbnail zooming-in region 525 shows most information that the scanning operator may be interested in, such as the ultrasonic image thumbnail that is zoomed in, the quality factor, the anatomical marker, etc. In such a zooming-in and displaying manner, the scanning operator can quickly acquire key information that the scanning operator intends to view without retrieving the ultrasonic image stored in the memory. Further, in such a configuration manner, what is mainly displayed by the user interface 500 of the display is still the current ultrasonic image 501, and the scan is not affected excessively. It should be understood that a variety of methods may be used to configure the first instruction. In an embodiment, a method may be single-clicking the ultrasonic image thumbnail 524 on the screen. In the teachings of the present application, other methods may also be used.

Figure 6:
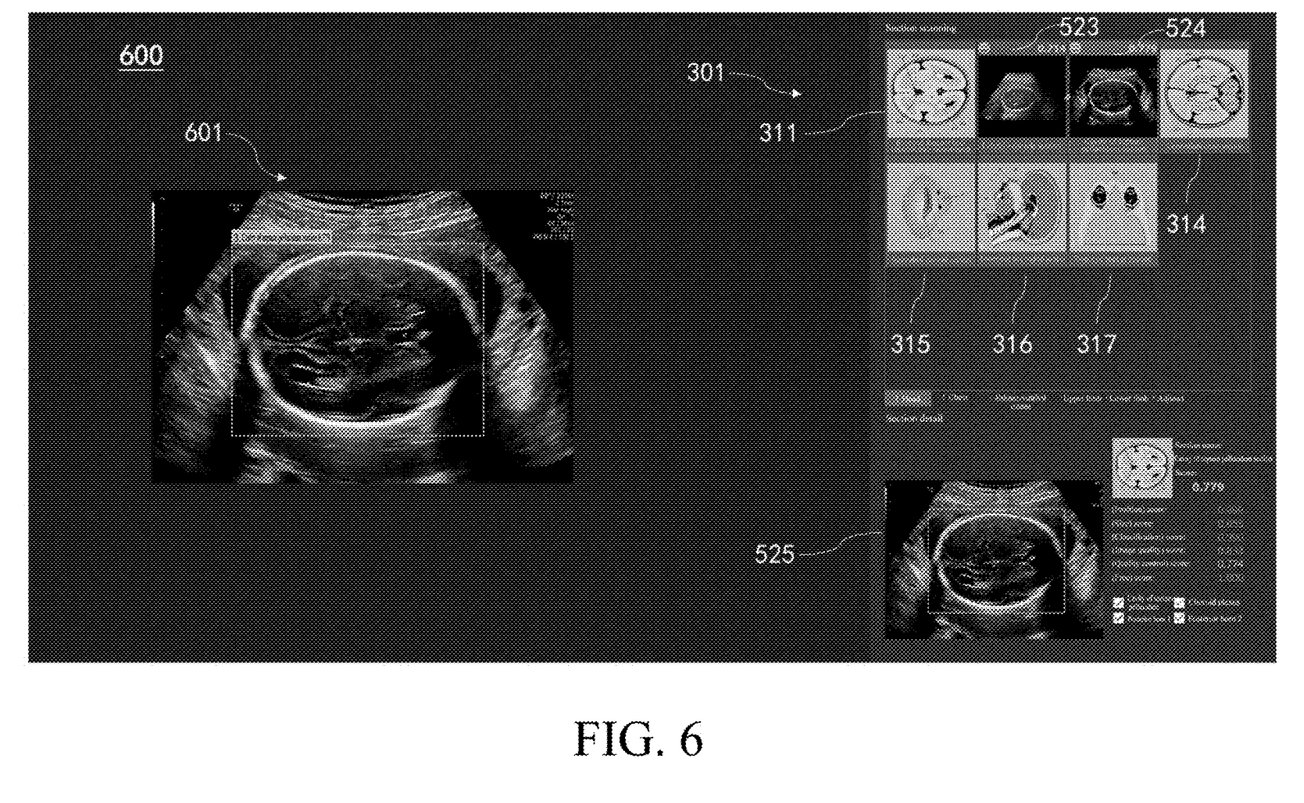
FIG. 6 is a schematic diagram of a variation of the graphical user interface of FIG. 5.

Further, the processor may be further configured to, in response to a second instruction, display the stored ultrasonic image of the anatomical plane of interest. The second instruction may be any manner different from the first instruction. In a non-limiting example, the ultrasonic image thumbnail 524 on the screen may be double-clicked. As shown in FIG. 6, FIG. 6 shows a schematic diagram of a variation of the graphical user interface of FIG. 5. In this case, the user interface 500 is updated to a user interface 600. That is, an ultrasonic image 601 of an anatomical plane of interest (e.g., a cavity of septum pellucidum section) is displayed.

In such a configuration manner, the scanning operator can easily view the stored ultrasonic image of the anatomical plane of interest. It can be determined whether image quality meets requirements of the scanning operator, and other operations, such as marking, can also be performed.

It will be appreciated that the above merely schematically illustrates the embodiments of the present application, but the present application is not limited thereto. For example, the order of execution between operations may be suitably adjusted. In addition, some other operations may also be added or some of these operations may be omitted. Those skilled in the art could make appropriate variations according to the above disclosure, rather than being limited by the above descriptions.

Some embodiments of the present invention further provide an ultrasonic imaging system, which may be as shown in FIG. 1, or may be any other system. The system includes: a probe, configured to acquire ultrasonic data; and a processor, configured to perform the method in any of the embodiments described above. The system further includes a display device configured to receive a signal from the processor for display.

In an example, the processor is configured to: generate a plurality of anatomical plane schematics, and cause a display to display the same, each one of the plurality of anatomical plane schematics respectively corresponding to a different anatomical plane of interest; acquire an ultrasonic image of the anatomical plane of interest; and automatically generate an ultrasonic image thumbnail of the anatomical plane of interest, automatically replace the anatomical plane schematic corresponding to the anatomical plane of interest with the ultrasonic image thumbnail, and cause the display to display the same.

Some embodiments of the present invention further provide a non-transitory computer-readable medium storing a computer program, wherein the computer program has at least one code segment, and the at least one code segment is executable by a machine so that the machine performs steps of the method in any of the embodiments described above.

Accordingly, the present disclosure may be implemented in the form of hardware, software, or a combination of hardware and software. The present disclosure may be implemented in at least one computer system in a centralized manner, or in a distributed manner in which different elements are distributed on a number of interconnected computer systems. Any type of computer system or other device suitable for implementing the methods described herein are appropriate.

The various embodiments may also be embedded in a computer program product that includes all features capable of implementing the methods described herein, and the computer program product is capable of executing these methods when being loaded into a computer system. The computer program in this context means any expression in any language, code, or symbol of an instruction set intended to enable a system with information processing capabilities to execute a specific function directly or after any or both of a) conversion into another language, code, or symbol; and b) duplication in a different material form.

The purpose of providing the above specific embodiments is to facilitate understanding of the content disclosed in the present invention more thoroughly and comprehensively, but the present invention is not limited to these specific embodiments. Those skilled in the art should understand that various modifications, equivalent replacements, and changes can also be made to the present invention and should be included in the scope of protection of the present invention as long as these changes do not depart from the spirit of the present invention.

The invention claimed is:
1. An ultrasonic imaging method, comprising:
generating a plurality of anatomical plane schematics, wherein each of the plurality of anatomical plane schematics corresponds to a different anatomical plane of interest, wherein the plurality of anatomical plane schematics includes a first anatomical plane schematic corresponding to a first anatomical plane of interest;

displaying the plurality of anatomical plane schematics on a display;

acquiring, with a probe, an ultrasonic image of the first anatomical plane of interest;

automatically generating, with a controller circuit, an ultrasonic image thumbnail of the first anatomical plane of interest; and automatically displaying the ultrasonic image thumbnail on the display in place of the first anatomical plane schematic.

2. The ultrasonic imaging method according to claim 1, wherein the first anatomical plane schematic is a graphical display of the first anatomical plane of interest.

3. The ultrasonic imaging method according to claim 1, wherein said acquiring the ultrasonic image of the first anatomical plane of interest comprises:

generating a real-time ultrasonic image based on an ultrasonic signal received by the probe; and automatically identifying at least one anatomical marker in the real-time ultrasonic image, and determining, based on the at least one anatomical marker, that the real-time ultrasonic image corresponds to the first anatomical plane of interest.

4. The ultrasonic imaging method according to claim 3, further comprising:

automatically determining a quality factor of each one of the at least one anatomical marker; and determining a quality level of the ultrasonic image of the first anatomical plane of interest on the basis of the quality factor of each anatomical marker; and causing the display to display the quality level.

5. The ultrasonic imaging method according to claim 4, further comprising:

acquiring an updated ultrasonic image of the first anatomical plane of interest;

automatically determining a quality level of the updated ultrasonic image;

automatically determining that the quality level of the updated ultrasonic image is higher than the quality level of the ultrasonic image;

automatically storing the updated ultrasonic image; and automatically displaying the updated ultrasonic image thumbnail on the display in place of the ultrasonic image thumbnail.

6. The ultrasonic imaging method according to claim 4, wherein the ultrasonic image includes a visual display of the quality level.

7. The ultrasonic imaging method according to claim 6, wherein the visual display of the quality level comprises a visual display of the quality factor of each anatomical marker.

8. The ultrasonic imaging method according to claim 1, further comprising:

automatically storing the ultrasonic image and the ultrasonic image thumbnail of the first anatomical plane of interest.

9. The ultrasonic imaging method according to claim 8, further comprising:

in response to a first instruction, zooming in and displaying the ultrasonic image thumbnail of the first anatomical plane of interest.

10. The ultrasonic imaging method according to claim 8, further comprising:

in response to a second instruction, displaying the stored ultrasonic image of the first anatomical plane of interest.

11. An ultrasonic imaging system, comprising:

a probe;

a display; and a controller circuit operatively connected to the probe and the display, wherein the controller circuit is configured to:

generate a plurality of anatomical plane schematics, wherein each of the plurality of anatomical plane schematics corresponds to a different anatomical plane of interest, wherein the plurality of anatomical plane schematics includes a first anatomical plane schematic corresponding to a first anatomical plane of interest;

cause the display to display the plurality of anatomical plane schematics;

control the probe to acquire an ultrasonic image of the first anatomical plane of interest;

automatically generate an ultrasonic image thumbnail of the first anatomical plane of interest; and automatically display the ultrasonic image thumbnail on the display in place of the first anatomical plane schematic.

12. The ultrasonic imaging system of claim 11, wherein the first anatomical plane schematic is a graphical display of the first anatomical plane of interest.

13. The ultrasonic imaging system of claim 11, wherein the plurality of anatomical plane schematics includes a second anatomical plane schematic corresponding to a second anatomical plane of interest, and wherein the controller circuit is further configured to:

control the probe to acquire a second ultrasonic image;

automatically determine that the second ultrasonic image corresponds to the second anatomical plane of interest;

automatically generate a second ultrasonic thumbnail image of the second anatomical plane of interest; and automatically display the second ultrasonic thumbnail image on the display in place of the second anatomical plane schematic, wherein the second ultrasonic thumbnail image is displayed at the same time as the ultrasonic image thumbnail.

14. The ultrasonic imaging system of claim 11, wherein the controller circuit is further configured to automatically identify at least one anatomical marker in the ultrasonic image.

15. The ultrasonic imaging system of claim 14, wherein the controller circuit is further configured to automatically determine that the ultrasonic image corresponds to the first anatomical plane of interest based on the at least one anatomical marker in the ultrasonic image.

16. The ultrasonic imaging system of claim 15, wherein the controller circuit is further configured to determine a quality factor for each of the at least one anatomical marker and use the quality factor determined for each of the at least one anatomical marker to calculate the quality level of the ultrasonic image.

17. The ultrasonic imaging system of claim 11, wherein the controller circuit is further configured to determine a quality level of the ultrasonic image using an artificial intelligence model.

18. The ultrasonic imaging system of claim 17, wherein the controller circuit is further configured to include a visual display of the quality level of the ultrasonic image in at least one of the ultrasonic image or the ultrasonic image thumbnail.

19. The ultrasonic imaging system of claim 18, wherein the controller circuit is configured to represent the quality level using a color.

20. A non-transitory computer-readable medium, storing a computer program having at least one code segment executable by a machine to cause the machine to perform steps comprising:
- displaying a plurality of anatomical plane schematics on a display;
- acquiring, with a probe, an ultrasonic image of a first anatomical plane or interest;
- automatically generating, with a controller circuit, an ultrasonic image thumbnail of the first anatomical plane of interest; and
- automatically displaying the ultrasonic image thumbnail on the display in place of a first anatomical plane schematic of the plurality of anatomical plane schematics.

* * * * *